(12) United States Patent
Sartawi

(10) Patent No.: US 12,396,857 B2
(45) Date of Patent: Aug. 26, 2025

(54) PROXIMALLY FITTING FEMORAL COMPONENT WITH ADJUNCTIVE SCREW FIXATION

(71) Applicant: Muthana M. M. A. S. Sartawi, Safat (KW)

(72) Inventor: Muthana M. M. A. S. Sartawi, Safat (KW)

( * ) Notice: Subject to any disclaimer, the term of this patent is extended or adjusted under 35 U.S.C. 154(b) by 1155 days.

(21) Appl. No.: 16/940,154

(22) Filed: Jul. 27, 2020

(65) Prior Publication Data
US 2020/0352725 A1 Nov. 12, 2020

Related U.S. Application Data

(62) Division of application No. 16/405,346, filed on May 7, 2019, now Pat. No. 10,758,356.

(51) Int. Cl.
*A61F 2/36* (2006.01)
*A61B 17/17* (2006.01)

(52) U.S. Cl.
CPC ........ *A61F 2/3609* (2013.01); *A61B 17/1753* (2013.01); *A61F 2/3672* (2013.01); *A61B 17/1725* (2013.01); *A61F 2002/3611* (2013.01); *A61F 2002/3625* (2013.01); *A61F 2002/365* (2013.01); *A61F 2002/3652* (2013.01)

(58) Field of Classification Search
CPC .................. A61F 2/3609; A61F 2/3672; A61F 2002/3611; A61F 2002/3625; A61F 2002/365; A61F 2002/3652; A61F 2/3662; A61F 2/4603; A61B 17/1753; A61B 17/1725
See application file for complete search history.

(56) References Cited

U.S. PATENT DOCUMENTS

| | | | |
|---|---|---|---|
| 5,108,449 A | 4/1992 | Gray | |
| 5,458,654 A | 10/1995 | Tepic | |
| 5,571,202 A | 11/1996 | Mathys, Sr. et al. | |
| 5,658,349 A | 8/1997 | Brooks et al. | |
| 5,776,194 A | 7/1998 | Mikol et al. | |
| 6,409,768 B1 | 6/2002 | Tepic et al. | |

(Continued)

OTHER PUBLICATIONS

Any identified foreign patents and/or publications were properly submitted in parent U.S. Appl. No. 16/405,346, filed May 7, 2019, the priority of which is claimed.

*Primary Examiner* — Javier G Blanco
(74) *Attorney, Agent, or Firm* — Nath, Goldberg & Meyer; Joshua B. Goldberg

(57) ABSTRACT

The proximally fitting femoral component with adjunctive fixation screws replaces a natural femoral head and proximal femur of a patient during a partial or total hip replacement. The femoral component includes an intramedullary stem having a proximal portion and a distal portion, a neck extending from the proximal portion, and a ball removably attached to a tip end of the neck, the ball forming a ball and socket joint with the acetabular cup of a hip prosthesis. Fixation screws may be installed in the proximal portion of the stem for added rotational and axial stability when necessary. An alignment device is removably attachable to the femoral component for aligning screw holes in cortical bone of the femur with holes or bores in the proximal portion of the stem. The fixation screws may extend in an anterior posterior or medial-lateral plane.

5 Claims, 5 Drawing Sheets

(56) References Cited

U.S. PATENT DOCUMENTS

| | | | |
|---|---|---|---|
| 7,247,171 B2 | 7/2007 | Sotereanos | |
| 7,641,698 B1 * | 1/2010 | Gibbs et al. | |
| 11,141,202 B1 * | 10/2021 | Haidukewych | A61B 17/1725 |
| 2003/0171819 A1 * | 9/2003 | Sotereanos | A61B 17/744 |
| | | | 623/908 |
| 2008/0009951 A1 | 1/2008 | Hodge | |
| 2014/0330390 A1 | 11/2014 | Liu et al. | |

* cited by examiner

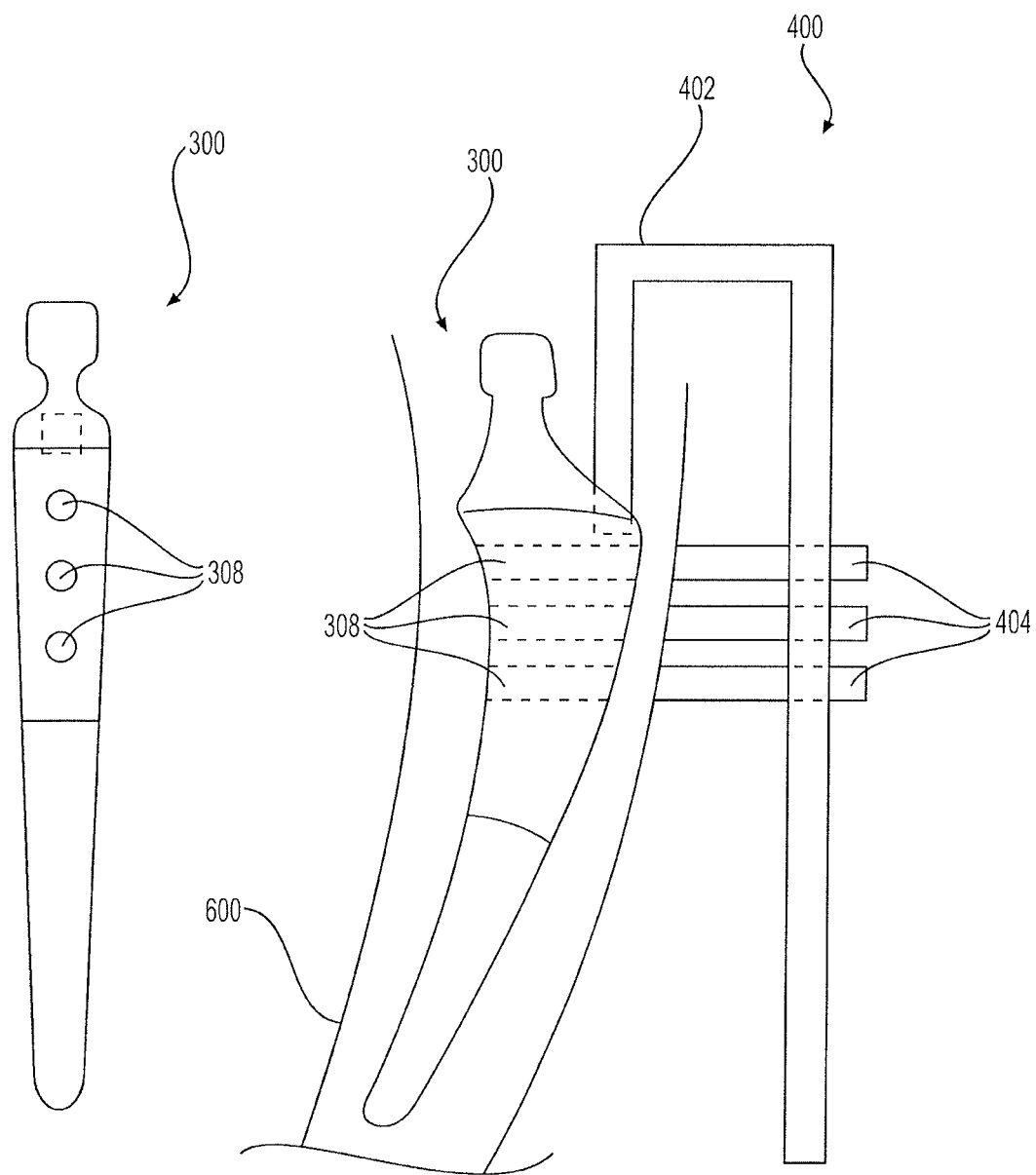
FIG. 4A  FIG. 4B

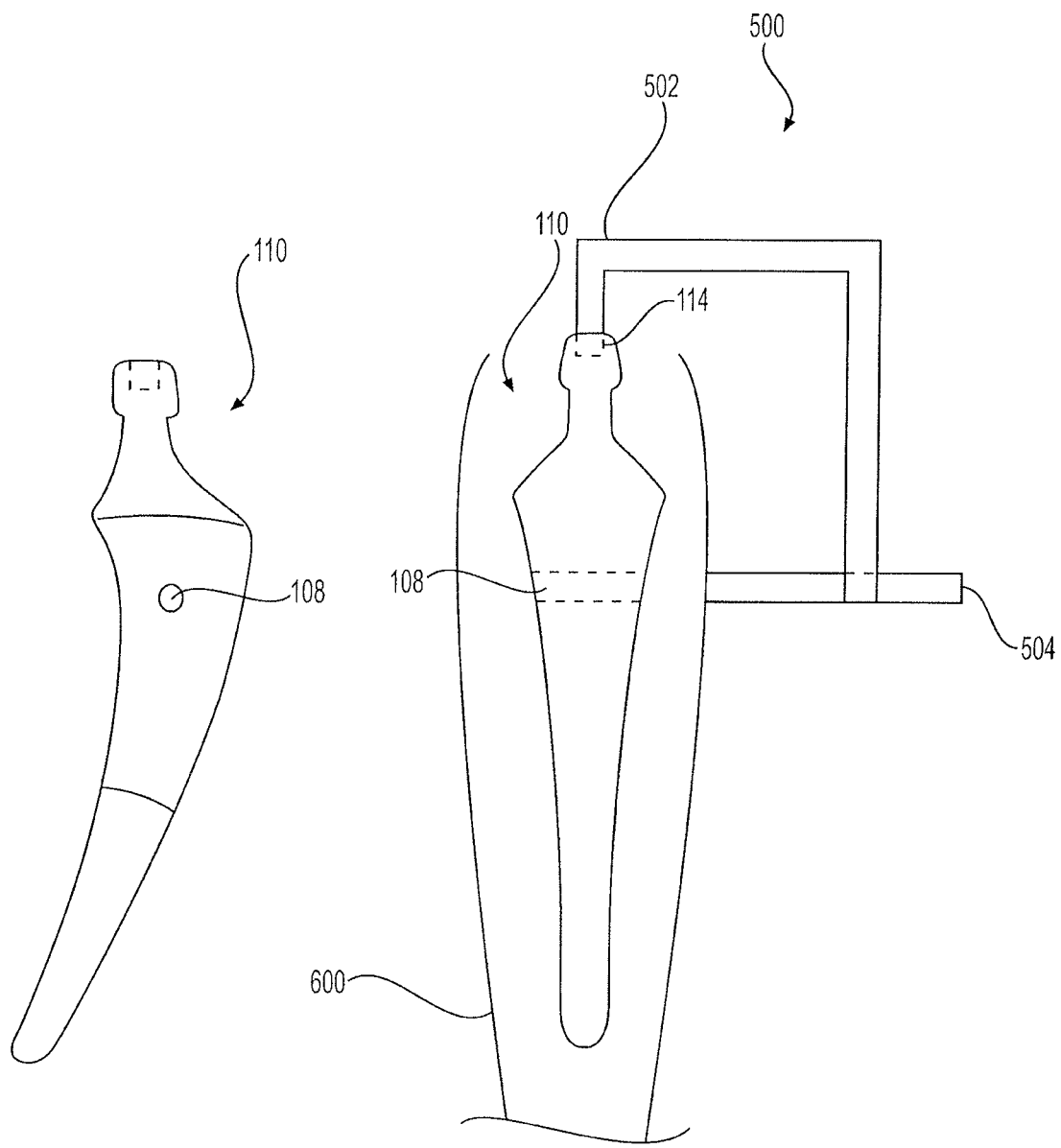
FIG. 5A  FIG. 5B

PROXIMALLY FITTING FEMORAL COMPONENT WITH ADJUNCTIVE SCREW FIXATION

BACKGROUND OF THE INVENTION

1. Field

The present disclosure relates to prosthetic implants, and particularly to a proximally fitting femoral component with adjunctive screw fixation for a hip replacement, which optionally accepts screws, as well as an associated method and tool for installation of the screws.

2. Description of the Related Art

Conventionally, artificial hip joints have been composed of a socket inserted into the pelvic bone and a femoral prosthesis, which has a stem and a spherical head at the end capable of rotatably engaging the socket.

In one approach, the stem, made of a metal such as stainless steel or cobalt-chromium alloy, is inserted into a femoral canal and fixed by using cementing compound between the stem and the canal wall. On the acetabular side, the socket is cemented to a pelvic bone, which receives the spherical head of the stem.

Particularly, the stem is inserted deeply within the elongated canal of the femur, and when the artificial joint is loaded, some difference in Young's modulus between the metal stem and the bone tissue causes different amounts of deformation, which leads to a sinking of the stem into the bone due to relaxation between the metal stem and the bone. This results in losing joint function through looseness between the members or, in the extreme case, separation of the stem from the femoral cavity.

Attempts have been made to prevent the looseness between the cement and bone or the metal stem. For example, the stem material has been made from titanium or titanium alloy instead of stainless steel or cobalt-chromium alloy in order to approximate the Young's modulus of the stem to that of the bone tissue. This attempt failed to completely resolve the looseness problem.

Another improvement has been attempted, in which the stem is formed such that the outside of the stem mirrors the inner dimensions of the bone canal, to make the gap between the stem surface and the bone canal as narrow as possible and then inserting the stem into the bone without the use of any cementing compound. It was, however, difficult to configure the stem into a shape that accurately duplicated the inner canal profile. Practically, sufficient products, except in the case of custom-ordered products, have not been available because of patients having great differences in inner femoral profiles.

Thus, a proximally fitting femoral component with adjunctive screw fixation solving the aforementioned problems is desired.

SUMMARY OF THE INVENTION

The proximally fitting femoral component with adjunctive screw fixation replaces a natural femoral head and proximal femur of a patient during a partial or total hip replacement. The femoral component includes a stem, which tapers inwards and bends medially towards its proximal end to match the shape of the medullary cavity of a femur for a press fit connection. Screw holes extend through the stem in the coronal (medial-lateral) and/or sagittal (anterior-posterior) planes to accept screws, which optionally assist in securing the stem to the femur. A targeting device may be used for guiding the practitioner's drill bit to the screw holes in the stem, which will be covered by the cortical bone of the femur. A neck extending from the stem accepts an artificial femoral head (ball) to be reduced into a patient's natural or artificial acetabular socket.

A method for installing a proximally fitting femoral component with adjunctive screw fixation in a hip joint prosthesis includes press fitting a femoral stem of the component into the femur. If the practitioner determines that the press fit will not provide enough stability, the stem may be screwed to the femur using screw holes in the stem. A targeting device, which may be temporarily attached to the top of the femoral stem, is used to align a drill bit with the holes in the stem that are covered by bone.

These and other features of the present disclosure will become readily apparent upon further review of the following specification and drawings.

BRIEF DESCRIPTION OF THE DRAWINGS

FIG. 4A is a lateral view of another embodiment of a proximally fitting femoral component with adjunctive screw fixation having a plurality of medial-lateral screw holes.

FIG. 4B is a schematic environmental front view of the femoral component of FIG. 4A, shown during installation with an attached targeting device.

FIG. 5A is a front view of the femoral component of FIG. 1, shown with the ball removed.

FIG. 5B is an environmental side view of the femoral component of FIG. 5A, shown during installation with an attached targeting device.

Similar reference characters denote corresponding features consistently throughout the attached drawings.

DETAILED DESCRIPTION OF THE PREFERRED EMBODIMENTS

The proximally fitted femoral component with adjunctive screw fixation replaces a natural femoral head and proximal femur of a patient during a partial or total hip replacement. The femoral component includes a stem, which tapers inward and bends medially towards its proximal end to match the shape of the medullary cavity of a femur for a press fit connection. Screw holes extend through the stem in the coronal (medial-lateral) and/or sagittal (anterior-posterior) planes to accept screws, which optionally assist in securing the stem to the femur. A targeting device may be used for guiding the practitioner's drill bit to the screw holes in the stem, which will be covered by the cortical bone of the femur. A neck extending from the stem accepts an artificial femoral head (ball) to be reduced into a patient's natural or artificial acetabular socket.

Figure 1:
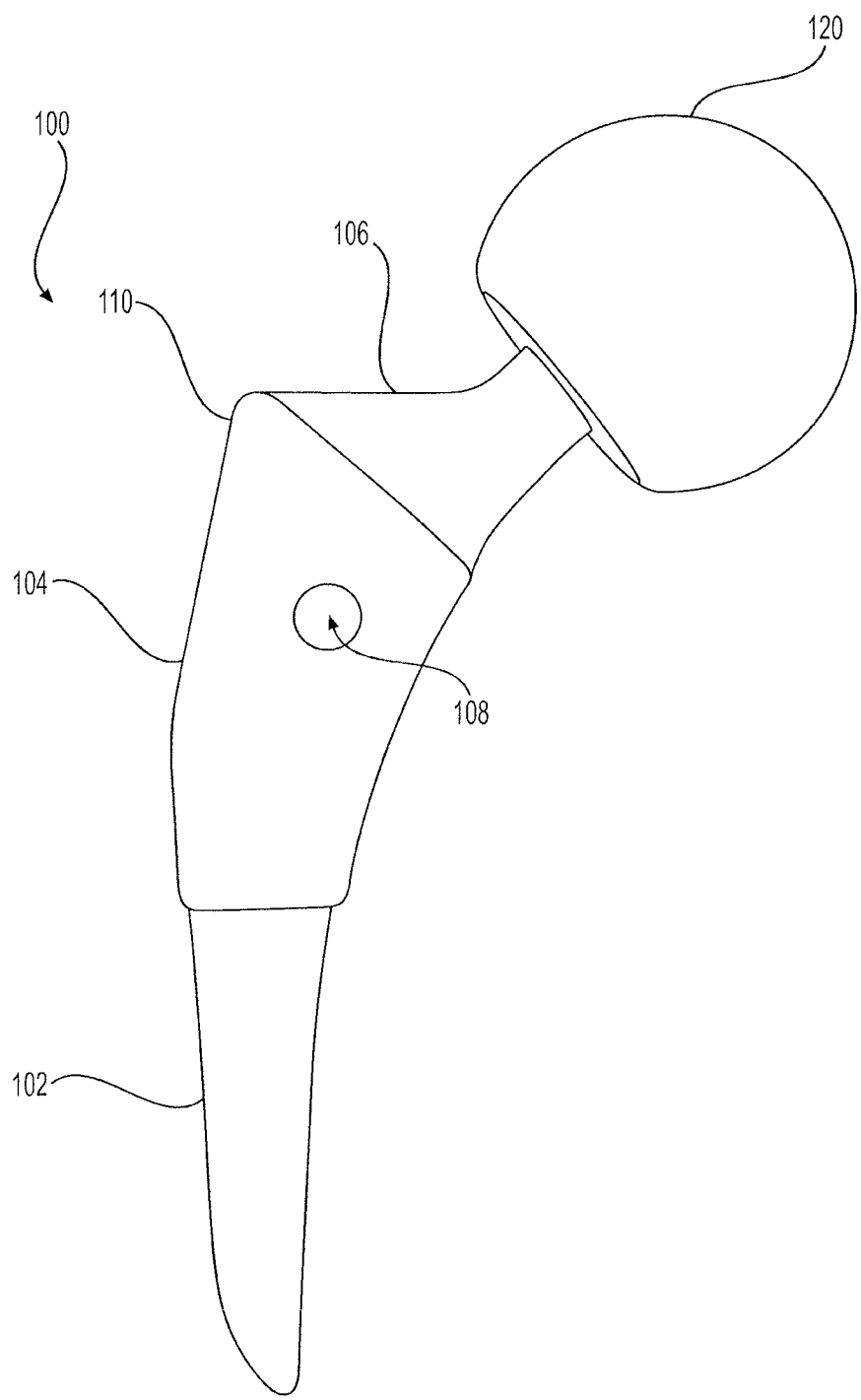
FIG. 1 is a front view of an embodiment of the proximally fitting femoral component with adjunctive screw fixation having an anterior-posterior screw hole.

FIG. 1 shows an embodiment of a femoral component 100 according to the present disclosure. The femoral component 100 includes a neck 106, a ball or head 120 removably attached to the neck, and an intramedullary stem 110 having a proximal portion 104 and a distal 102 portion, the intramedullary stem being adapted for insertion into the medullary cavity of a femur. During a hip replacement procedure, the natural femoral head is cut off the femur, which exposes the femur's medullary cavity. The medullary cavity is filled with cancellous (spongey) bone, which should be reamed out to provide room for the stem 110 to be inserted. A properly fitted stem 110 will be directly contacting the outer cortical bone, which is much stronger and harder than cancellous bone, and therefore will provide a better anchoring point for the stem 110. In some cases, a small amount of cortical bone at the proximal portion of the medullary cavity will be removed so that the cavity matches the exact shape of the proximal portion 104 of the stern 110 to provide better support and bone ingrowth. Accordingly, it is desirable for the stem 110 to be dimensioned and configured to match the shape of the femoral cavity created by the cortical bone. The stem 110 is shown in the figure as an exemplary embodiment. Other stem shapes known in the art may also be used. The stem 110 may be made from any material known in the art for making femoral stems, such as titanium, cellular titanium, stainless steel, or any inert or biocompatible metal. The stem 110, and particularly the proximal portion 104 of the stem 110, may include a coating to enhance securement to the bone by bone growth, such as a porous coating.

The proximal portion 104 of the stern 110 is designed to seat within the epiphysis portion of the femur. Since this is the largest portion of the medullary canal, with the thickest cortical bone, the proximal portion 104 of the stem 110 will have the largest cross section to fill the cavity. As seen in FIG. 1, in some embodiments, the transition from the distal 102 to proximal 104 portions of the stem may not be a constant taper, but rather a step or shoulder marks the transition. This feature results in the primary force of attempting to press fit the stem 110 into the femur to be directed at the thicker cortical bone in the epiphysis portion of the cavity. In addition, the proximal portion 104 may have a thicker porous coating to allow for greater bone ingrowth, aided by the tighter fit. The distal portion 102 of the stern tapers into a point for insertion deep into the medullary cavity. A neck extends from the stem 110 at an oblique angle for attaching the ball 120 that acts as a femoral head, permitting the ball 120 to rotate in the hip socket or acetabular cup of a hip prosthesis so that the femoral component 100 can pivot lateral to and inferior from the hip in the manner of the natural femoral motion. The neck is shaped to apply an angular and medial offset to the attached ball 120. The offset positions the ball at an orientation that resembles the natural shape of the femur and femoral head so that natural movement may be achieved by that patient after the procedure. The transition between the neck 106 and the proximal portion 104 of the stem 110 opposite the neck 106 defines a trochanteric eminence, which may bear against cortical bone at the level of the greater trochanter when the stern 110 s press fit into the medullary cavity.

In many cases, femoral-components loosen due to subsidence (a downward sinking or settling into the bone). In order to combat potential loosening of the stem 110 in the medullary cavity, the stem 110 may include a transversely extending bore or screw hole 108 through or into the proximal portion 104 of the stem 110 for accepting a fixation screw 112 that extends through the cortical bone of the femur 600. The screw 112 extending through or into the screw hole 108 will provide interference anchoring, through interference of the bone 600 around the bone hole in which the screw 112 is inserted, in addition to the friction anchoring provided by the press fitting of the stem 110 in the cavity. Accordingly, the screw 112 will add additional rotational and axial stability to the stem-femur connection. The screw 112 may be used when the size of the femur's 600 medullary cavity is between sizes of femoral stems. Instead of risking bone fracture by forcing a slightly larger stem, a smaller stem can be used with a screw 112 for adequate securement to the femur 600 until the stern becomes fixed by growth of bone tissue through the porous coating on the proximal portion 104 of the femoral component 100. The determination for adding screws 112 may be made by the practitioner during the operation, once the stem 110 is fully installed in the femur 600. If the practitioner believes the stem 110 has a high risk of loosening, screws 112 may be added.

In FIG. 1, it will be noted that the femoral component 100 has an anterior face viewed in the front view of FIG. 1 and a posterior face directed rearward and not seen in FIG. 1. The lateral aspect of the femoral component shown in FIG. 1 has convex curvature, and the medial aspect has concave curvature, the trochanteric eminence projecting laterally and the neck 106 extending medially.

Figure 2:
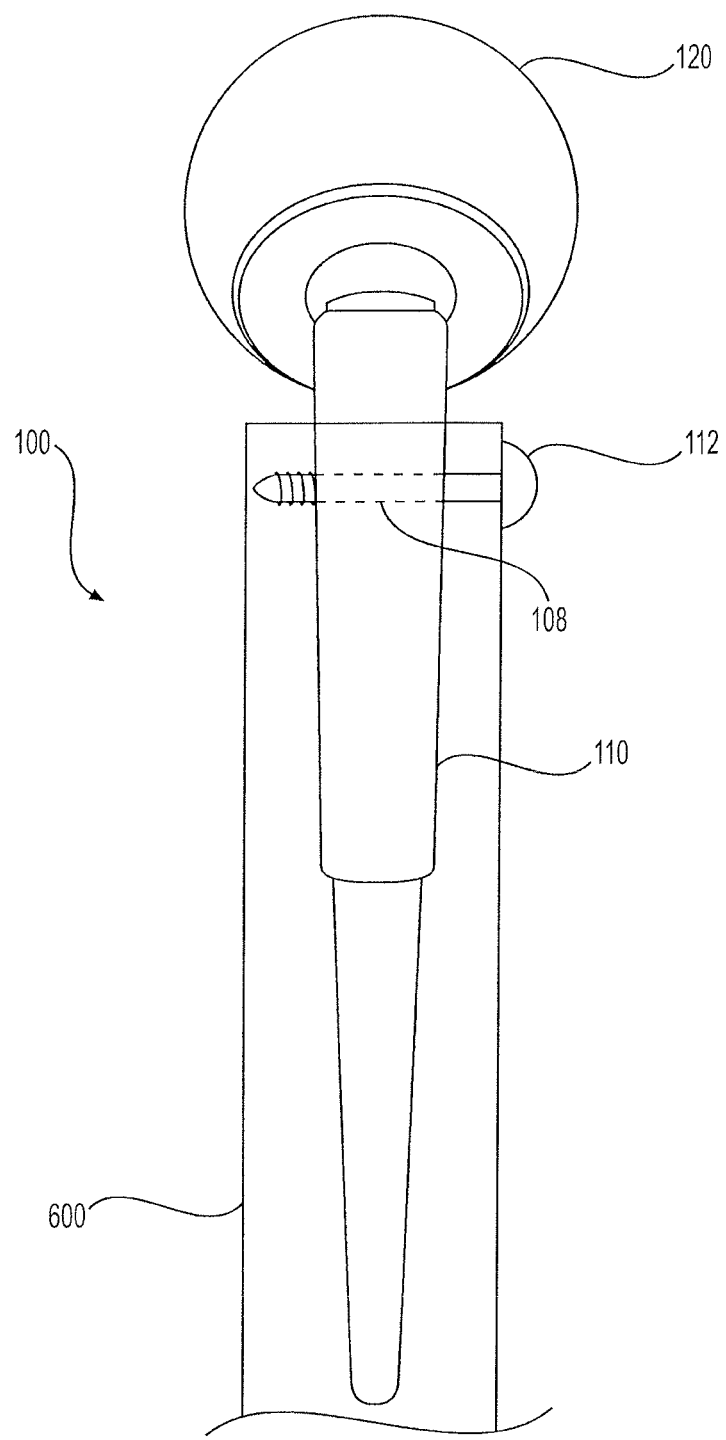
FIG. 2 is an environmental side view of the femoral component of FIG. 1, shown inserted into a prepared femur and fixed with a screw.

As seen in the embodiment of FIGS. 1 and 2, the stem 110 may include only a single screw hole 108, which is oriented in an anterior-posterior direction. In different embodiments, the screw holes 108 may be oriented in a medial-lateral direction, or in both medial-lateral and anterior-posterior directions. Screws 112 can be inserted from either side of the screw holes 108, depending on which side is most accessible to the surgeon. Accordingly, for medial-lateral holes, the screws 112 can run medially-to-laterally or laterally-to-medially, and for the anterior-posterior holes, the screws 112 can run anterior-to-posterior or posterior-to-anterior. Some embodiments may include screw holes extending in the transverse plane at an angle between the anterior and lateral directions. The orientation of the holes 108 and screws 112 may be determined based on locations that are easily accessible during the surgery. For additional fixation, multiple screws 112 and associated screw holes 108 may be used. In cases that require multiple screws 112, the orientations may be offset to prevent stress propagation in portions of the femur 600 due to the screws 112 and associated holes in the femur 600.

Figure 3:
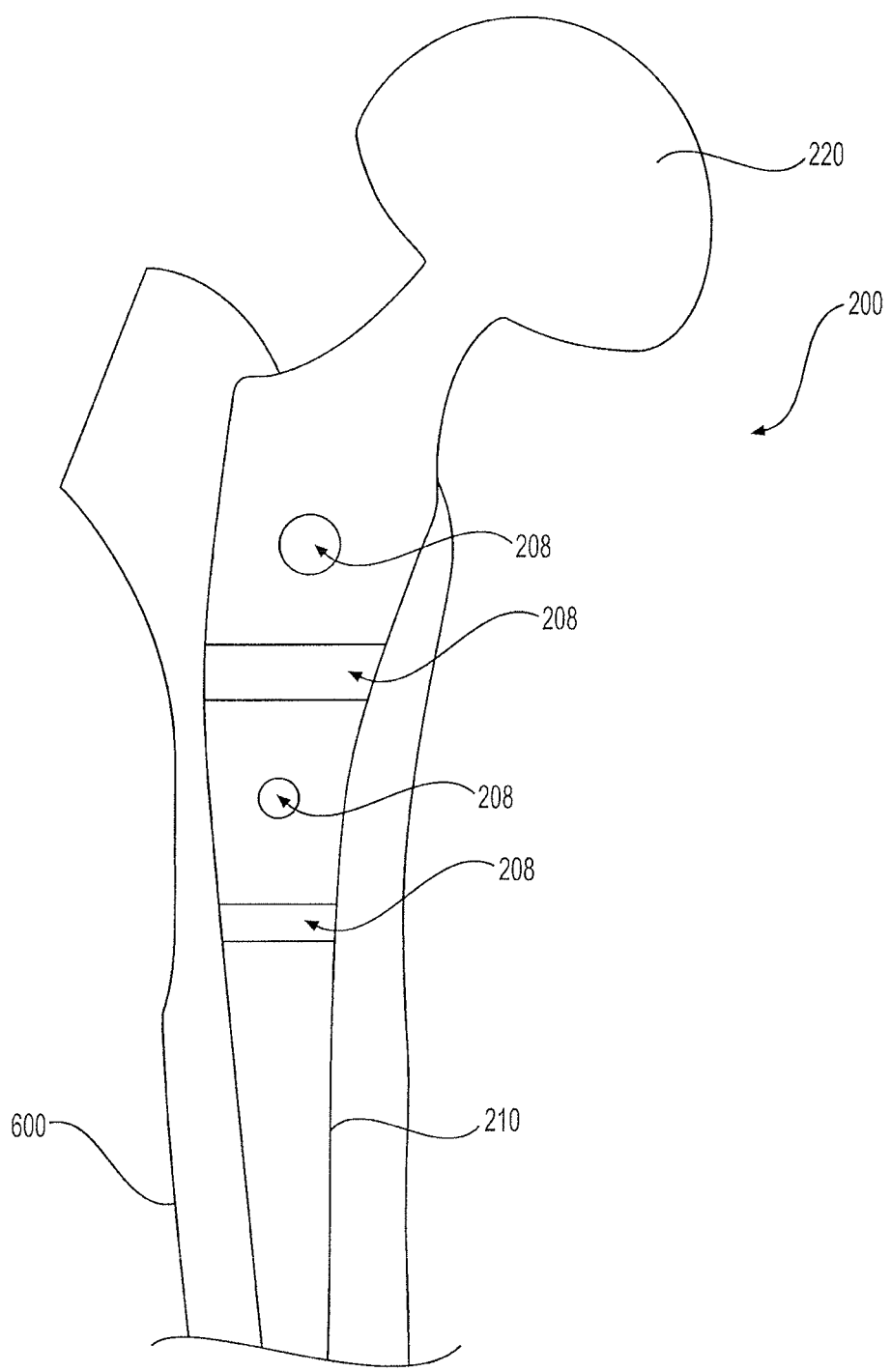
FIG. 3 is a schematic environmental front view of another embodiment of a proximally fitting femoral component with adjunctive screw fixation having both anterior-posterior and medial-lateral screw holes.

Screw hole 208 location may be selected based on bone strength/density at different locations of the femur 600, as well as ease of access during the surgery. Additionally, screw holes 208 may be separated along the length of the stem 210 to prevent a grouping of stress risers caused by the screws when loaded, which may cause the femur 600 to fracture. In some cases, a generic stem 210, as seen in FIG. 3, can be used, which has multiple screw holes 208 at different locations and orientations. The generic stem allows the practitioner to select the amount, location, and orientation of the screws 112 after the stem has been press fit into the femur 600. In some embodiments, different size screw holes 208 and associated screws 112 may be used on a stem 210. The sizes may be determined based on the bone 600 and stem 210 strength at the location of the hole.

Screw type 112 and shape may be selected by the practitioner based on the circumstances of the procedure. In some embodiments, screw diameter and associated screw hole 108 size may be in the range of 3.5 mm to 6.5 mm. A larger diameter screw 112 may provide better securement to the bone 600 and have a lower chance of breaking. However, the larger screw 112 will require a larger hole in the bone 600 and the femoral stem 110, which may result in each having less strength and a larger concentration of stress.

In some embodiments, bicortical screws 112 may be used. Bicortical screws will extend through the width of the bone, including the cortical bone on each side of the medullar cavity, as seen in FIG. 2. The bicortical screws 112 may be partially threaded, as seen in FIG. 2, or fully threaded. The partially threaded screws 112 may provide superior fixation, since the portion extending through and engaging the stem 110 will have a full circumference, instead of screw threads, which may result in a more secure fit. In addition, only the terminal end of the screw 112 will be screwed into the bone, thus compressing the bone onto the stem 110 for greater frictional securement and bone ingrowth. In some embodiments, unicortical screws may be used, which only extend through the cortical bone on one side of the femur. When using unicortical screws, the screw holes in the stem 110 may be blind holes.

FIG. 4B shows an embodiment of a targeting device 400 for aligning a drill bit with lateral-medial screw holes 308 in the femoral component 300 of FIG. 4A. FIG. 4B shows the femoral component 300 installed into the medullary cavity of a femur 600. After the component 300 is press fit into an installed position in the medullary cavity of the femur 600, the location of the screw holes 308 will be hidden by the surrounding bone 600. The targeting device 400 may be used to indicate the hole 308 locations and to guide a drill bit into the holes 308. As seen in FIG. 4B, the targeting device 400 includes a hook or U-shaped alignment member 402 having three attached drill guides 404 on the longer leg of the device 400. The alignment member 402 is designed so that the drill guides 404 are aligned with the screw holes 308 of the stem 300 when the insertion end of the U-shape is inserted into a recess or port 314 in the trochanteric eminence of the component 300 (the head or ball being removed), e.g., by using the targeting device 400 to pre-drill the screw holes in the femoral component 300 before the component 300 is press fit into the medullary cavity. The port 314 may be designed to accept the alignment member 402 at only one angular and spatial orientation. Accordingly, once the alignment member 402 is fully inserted into the port 314, the practitioner will be assured that the drill guides 404 are aligned with the screw holes 308 in the component 300, and he/she may then drill the holes into the bone. In some embodiments, the port 314 may be designed to accept the alignment member 402 at multiple orientations so that it may be used for screw holes having different angular orientations. The drill guides 404 may define lumens having the same diameter opening as the screw holes 308 in the component 300. Accordingly, if the stem has screw holes of different sizes, the drill guides will have lumens of different sizes.

FIGS. 4A and 4B showed a femoral component 300 and targeting device for medial-lateral (or lateral-medial fixation screws. FIGS. 5A-5B show an embodiment of a femoral stem 110 and a targeting device 500 for aligning a drill bit with an anterior-posterior screw hole 108 for an anterior approach, once the femoral stem 110 is installed into the medullary cavity of a femur 600. Similar to the targeting device 400 for lateral-medial screw holes, the targeting device 500 includes a U-shaped hook or alignment member 502. The alignment member 502 is designed to be accepted into a port 114 on top of the tip or end of the neck 106, the ball 120 (shown in FIG. 1) being removed. Once accepted into the port 114, the drill guide 504, attached to the alignment member 502, will direct a drill bit inserted therein towards the screw hole 108 in the stem 110.

The following exemplary steps may be undertaken to install the femoral component using an anterior approach. The practitioner may perform the routine steps of inserting a cementless proximally fitted femoral stem into the femur, trying to achieve the best press fit fixation by broaching the medullary canal of the femur sequentially up to the size that gives the best rotational and axial stability. The practitioner may then proceed with the construct by attaching an appropriate trial femoral stem and head, and then reducing the hip to check for final stability, offset, and leg lengths. The hip may then be dislocated and the trial stem with the attached trial head and neck may be removed. The true femoral prosthesis 100 may then be opened, fully inserted and checked for final stability.

Prior to impacting the true femoral head in place and reducing the hip, if the practitioner feels the need to add more stability to the press fit femoral stem, he/she can then attach the targeting device anteriorly, as illustrated in FIGS. 5A-5B, and insert one or more screws to stabilize the stem. FIGS. 1-5B show either one or three screws, but two screws or more than three screws may also be used. The number of adjunctive screw sites will depend on the concern of stress risers in the stem when loaded. This will be less of a concern with only one screw and more of a concern with more screws.

The drill bit corresponding to the screw 112 diameter may then be inserted through the drill guide of the targeting device and drilled through the femoral cortex in alignment with the screw hole(s) in the stem. A depth gage may then be used to determine screw length, and the final screw may then be inserted. The same steps may be repeated for more screws. The targeting device may then be detached and the femoral head impacted and reduced in the acetabular cup.

Although these exemplary steps refer to the sequence for an anterior approach to the hip, the same steps may be followed with a posterior approach if the targeting device is attached posteriorly and the screw(s) are oriented back-to-front instead. Similar steps may be used to place side-to-side screws as well. For example, the targeting device may be attached medially or laterally and a drill guides can extend to the side to allow lateral-to-medial or medial-to-lateral screw placement.

It is to be understood that the proximally fitted femoral component with adjunctive screw fixation is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for implanting a proximally fitting femoral component of a hip joint prosthesis, comprising the steps of:
   providing a proximally fitting femoral component comprising:
   an intramedullary stem having a proximal portion and a distal portion extending from the proximal portion, wherein the proximal portion has a terminal portion, the stem being dimensioned and configured for insertion into a medullary cavity of a femur with the proximal portion press fit in the cavity;
   a neck extending from the terminal portion of the proximal portion of the stem at an oblique angle, the neck having a proximal end and a distal end, a trochanteric eminence formed at the junction between the distal end of the neck and the terminal portion of the proximal portion of the intramedullary stem, wherein the trochanteric eminence has a port defined at a proximal-most end of the proximal end of the neck therein; and a femoral head removably attached to the proximal end of the neck, the femoral head size and configured for forming a ball and socket joint with a hip prosthesis;

removing a femoral head of a femur to expose a femoral canal;

successively broaching the femoral canal with femoral stems of progressively increasing size to form a medullary cavity dimensioned and configured for providing optimal rotational and axial stability for the intramedullary stem of the proximally fitting femoral component;

providing an alignment device having a U-shaped body including a short leg forming a hook attachable to the port in the proximal end of the neck and a parallel long leg having at least one drill guide tube extending therefrom;

attaching the alignment device to the proximally fitting femoral component with the at least one drill guide tube of the alignment device positioned for drilling at least one transverse bore into the proximal portion of the intramedullary stem of the proximally fitting femoral component to provide additional stability;

drilling the at least one transverse bore into the proximal portion of the intramedullary stem of the proximally fitting femoral component;

detaching the alignment device from the proximally fitting femoral component;

inserting the intramedullary stem of the proximally fitting femoral component into the medullary cavity formed in the femur to provide a press fit of the proximally fitting femoral component and to provide rotational and axial stability;

attaching the alignment device to the port in the trochanteric eminence of the proximally fitting femoral component with the at least one drill guide tube bearing against the femur and aligned with the at least one transverse bore in the proximal portion of the intramedullary stem;

using the at least one drill guide tube to drill a hole through cortical bone of the femur aligned with the at least one transverse bore;

detaching the alignment device from the proximally fitting femoral component;

threading a bone screw through the hole in the cortical bone and into the at least one transverse bore in the intramedullary stem of the proximally fitting femoral component in order to fix the femoral component to the cortical bone of the femur;

attaching the femoral head to the neck of the proximally fitting femoral component; and reducing the femoral head in an acetabular cup of the hip prosthesis.

2. The method for implanting a proximally fitting femoral component according to claim 1, wherein said screw is oriented in an anterior-posterior plane.

3. The method for implanting a proximally fitting femoral component according to claim 1, wherein said screw is oriented in a medial-lateral plane.

4. The method for implanting a proximally fitting femoral component according to claim 1, wherein said step of threading a bone screw comprises threading a bicortical screw through cortical bone on both sides of the proximally fitting femoral component.

5. The method for implanting a proximally fitting femoral component according to claim 1, wherein said step of threading a bone screw comprises threading a unicortical screw through cortical bone on only one side of the proximally fitting femoral component and into the proximal portion of the intramedullary stern of said proximally fitting femoral component.

* * * * *